United States Patent
Goto et al.

(10) Patent No.: US 9,839,498 B2
(45) Date of Patent: Dec. 12, 2017

(54) MULTILAYER RESIN MATERIAL FOR DENTAL MILLING AND MACHINING

(71) Applicant: SHOFU INC., Kyoto (JP)

(72) Inventors: Masanori Goto, Kyoto (JP); Toshio Kitamura, Kyoto (JP); Mitsuji Teramae, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/362,867

(22) Filed: Nov. 29, 2016

(65) Prior Publication Data

US 2017/0151041 A1 Jun. 1, 2017

(30) Foreign Application Priority Data

Nov. 30, 2015 (JP) .................. 2015-234209

(51) Int. Cl.
*A61C 13/00* (2006.01)
*A61C 13/09* (2006.01)
*A61C 13/08* (2006.01)
*A61C 5/10* (2006.01)

(52) U.S. Cl.
CPC ............ *A61C 13/0022* (2013.01); *A61C 5/10* (2013.01); *A61C 13/082* (2013.01); *A61C 13/09* (2013.01)

(58) Field of Classification Search
None
See application file for complete search history.

(56) References Cited

U.S. PATENT DOCUMENTS

| | | | | |
|---|---|---|---|---|
| 2002/0022677 A1* | 2/2002 | Teramae | ............... | A61K 6/0023 523/113 |
| 2010/0209879 A1* | 8/2010 | Fukuchi | ................. | A61K 6/083 433/219 |
| 2013/0081272 A1* | 4/2013 | Johnson | ............. | A61C 13/0004 29/896.1 |
| 2015/0094396 A1* | 4/2015 | Nakatsuka | ........... | A61K 6/0005 523/116 |
| 2015/0315086 A1* | 11/2015 | Kawamura | .......... | A61K 6/0005 501/134 |

* cited by examiner

*Primary Examiner* — Tahseen N Khan
(74) *Attorney, Agent, or Firm* — Wenderoth, Lind & Ponack, L.L.P.

(57) ABSTRACT

To provide a multilayer resin material for dental milling and machining, comprising an inorganic filler in a content of 40% by weight or more and a plurality of layers different in transparency and color tone from each other, wherein the thickness of the uppermost layer (U) and the thickness of the lowermost layer (L) are each 1 mm or more, the contrast ratios (uppermost layer: $C_U$, lowermost layer: $C_L$) as indices for the transparency of the uppermost layer (U) and the transparency of the lowermost layer (L) satisfy the following relations:

$$0.30 \leq C_U \leq 0.60$$

$$0.55 \leq C_L \leq 0.90$$

$$C_U < C_L$$

and the chromaticities (uppermost layer: $L_U \cdot a_U \cdot b_U$, lowermost layer: $L_U \cdot a_U \cdot b_L$) based on the L*a*b* colorimetric system as the indices of the color tones in the uppermost layer (U) and the lowermost layer (L) satisfy the following relations:

$$60 \leq L_U \cdot L_L \leq 80$$

$$-3 \leq a_U \cdot a_L \leq 2$$

$$0 \leq b_U \cdot b_L \leq 30$$

18 Claims, No Drawings

MULTILAYER RESIN MATERIAL FOR DENTAL MILLING AND MACHINING

This application is based on and claims the benefit of priority from Japanese Patent Application Serial No. 2015-234209 (filed on Nov. 30, 2015), the contents of which are hereby incorporated by reference in their entirety.

BACKGROUND OF THE INVENTION

Field of the Invention

The present disclosure relates to a resin material for dental milling and machining constituted with a plurality of layers different from each other in transparency and color tone, for preparing dental prosthetic devices (crowns, bridges).

Description of the Related Art

As a dental prosthetic treatment, there has hitherto been adopted a technique to apply to a tooth loss portion a dental crown prepared by casting of an alloy material. This is a prosthetic device preparation technique in which a dental caries portion of a tooth is removed by milling, the negative mold of the remaining tooth is taken with an impression material, plaster is poured into the negative mold to prepare a tooth model, the tooth loss is restored on the tooth model with wax, and the form of the wax is replaced with an alloy by the lost wax method to prepare a prosthetic device.

As a prosthetic device, in addition to an alloy material, a ceramic material or a resin material is sometimes used. When these materials are used, generally adopted is a method in which the prosthetic devices are also prepared by piling each of these materials on the plaster model restoring the lost tooth.

Recently, owing to the development of the dental CAD/CAM technique, the following technique has come to be used: the plaster model reproducing a lost tooth is optically scanned to produce a digital data of the lost tooth on a computer, a digital data of a prosthetic device is produced on the basis of the digital data of the lost tooth, and the prosthetic device is prepared by milling and machining a material on the basis of the digital data of the prosthetic device. For such a preparation of a prosthesis on the basis of the CAD/CAM technique, various materials (such as an alloy, a ceramic, and a resin) are required to be molded beforehand into block bodies (such as a rectangular shape and a disk shape).

With respect to the color tone of a prosthetic device, an alloy material is greatly different in color tone from natural teeth and accordingly aesthetically unsuitable for prosthetic devices. For the preparation of prosthetic devices conforming in color tone to natural teeth and high in aesthetic performance, ceramic materials and resin materials are used. In those conventional methods in which materials are manually piled on plaster models, it is possible to reproduce the same color tone as the color tone of natural teeth by piling ivory-colored materials or enamel-colored materials in layers.

In contrast, in order to prepare prosthetic devices high in aesthetic performance by using materials molded in block shapes for the CAD/CAM technique, it is required to arrange beforehand in the block bodies the same ivory color and the same enamel color as the color of natural teeth.

CITATION LIST

PTL 1: National Publication of International Patent Application No. 1992-505113
PTL 2: International Publication No. WO 2002/09612
PTL 3: Japanese Patent Laid-Open No. 2004-35332
PTL 4: National Publication of International Patent Application No. 2011-528597
PTL 5: Japanese Patent Laid-Open No. 2012-130798
PTL 6: Japanese Patent Laid-Open No. 2014-161440
PTL 7: Japanese Patent Laid-Open No. 2014-218389
PTL 8: International Publication No. WO 2015/051095

National Publication of International Patent Application No. 1992-505113 provides a block body having a layer structure including a plurality of layers, and describes a method for preparing a tooth shape by milling and machining this material. The foregoing document describes, for example, the imitation of the form of a natural tooth adopted in the structure of layers, and the imitation of the ivory color or the enamel color adopted in the color tone of the layers. However, the practical application of the foregoing technique requires a high level production technique to impart curved layer structure to the block body, and is anticipated to be costly.

International Publication No. WO 2002/09612 describes a technique of a block having a layer structure including a plurality of layers. This technique is characterized in that the color tones of the respective layers are made to imitate the ivory color or the enamel color, and the layer structure is curved. The prosthetic device obtained by milling and machining of the block body due to the foregoing technique approximates the layer structure of a natural tooth. However, the technical description of the color tone design of each layer in the foregoing document is limited only to the imitation to the ivory color and the enamel color. In the design of the curved layer structure, the layer structure based on the patterned curved surfaces is assumed in consideration of practical application. However, the patterned layer structure requires a certain degree of multilayer (four to five layers) in order to reproduce the color tone of a natural tooth.

Japanese Patent Laid-Open No. 2004-35332 describes a ceramic block technique in which two or more materials having different color tones are mixed to prepare a prosthetic device. Specifically, the prosthetic device is a ceramic block having a layer structure including a plurality of layers, wherein an intermediate color is prepared by mixing two or more materials having different color tones, and while the color tone of the intermediate color is being varied, layer structures are formed. However, the foregoing technique is a technique specialized to powder materials capable of being easily mixed. The description related to the color tone design is limited to the description of the imitation of natural teeth, and no specific construction of techniques is performed.

National Publication of International Patent Application No. 2011-528597 describes a forming member composed of two components different in color tone. Specifically, the forming member is composed of an ivory-color component layer and an enamel-color component layer, and the shape of the interface between the respective component layers is prescribed in detail as a parabolic shape. Such a prescription of the interface shape as a parabolic shape allows an ivory color structure and an enamel color structure approximating a natural tooth to be imparted to the prosthetic device subjected to milling and machining. For the practical application of the foregoing technique, a method using a die/mold having a parabolic shape is quoted. However, this method requires a sequential molding of a first layer and a second layer, accordingly usable materials are limited, and there may occur a large number of technical problems related to molding. In the foregoing document, there is no knowledge about the layer structure having three or more layers.

Japanese Patent Laid-Open No. 2012-130798 describes a multicolored compact having a layer structure. The technique described in the foregoing document is characterized in that there are two middle layers different in color between two main layers having different colors, the color variation of these middle layers is in the direction opposite to the color variation direction of the main layers, each of the middle layers is as thin as 0.2 to 0.4 mm in thickness, and thus, the color variation of the whole of the compact looks like transitional. This utilizes the color vision illusion of an observing human, and thus, the color variation in the whole of the layer structure is perceived continuously. However, the foregoing technique requires at least four layers in the layer structure of the compact, and preferably a layer structure having approximately eight layers is desired. In a compact having a limited thickness in the preparation of a dental crown prosthetic device, the impartment of many layer structures leads to a high difficulty in technical aspect, and is disadvantageous in the aspect of production cost.

Japanese Patent Laid-Open No. 2014-161440 describes a resin-based block composed of a resin layer for dentin restoration and a resin layer for enamel restoration. The foregoing document states that by prescribing the contrast ratio and the light diffusibility of the resin layer for dentin restoration, a reproducibility of the color tone similar to the color tone of a natural tooth is obtained even in a simple two-layer structure block. However, for the implementation of the foregoing technique requires mixing of light diffusing particles in the dentin layer. The requirement for the light diffusing particles is such that the average particle size is 1 to 50 μm, and the diffusing particles have a predetermined relation with the refractive index of the resin component. Accordingly, the light diffusing particles are restricted with respect to the component composition, and the use of a filler having an average particle size of a few microns also leads to poor surface polishing property. Moreover, there is caused a state in which the resin layer for dentin restoration and the resin layer for enamel restoration are different in the component ratios, and accordingly apprehended is the generation of the residual stress due to the difference in polymerization rate/polymerization shrinkage rate between the respective layers during production of the block body.

Japanese Patent Laid-Open No. 2014-218389 describes a technique for the color tone of a zirconia sintered body. Specifically, the technique is characterized in that the color tones of two points in the sintered body are respectively prescribed, and the increase-decrease tendency between the two points is not varied. However, the foregoing technique is a technique for allowing the color tone of the zirconia material having low transparency to imitate the color tone of a natural tooth having translucency, and cannot be applied to a resin material having a translucency equivalent to the translucency of a natural tooth.

International Publication No. WO 2015/051095 describes a blank for milling and machining, formed of a two-layer structure or a three-layer structure. Specifically, this is a technique to express transitionally the color tone variation of the boundary surface(s) between the layers by minutely prescribing the curve design of the boundary surface(s) between the layers. In the color tone design of each layer in the foregoing technique, the relationship between the transparency and the color tone of each layer is considered. With respect to the design of the transparency and the color tone of each layer, only the concept is stated and no clear setting is presented. In other words, neither design of the transparency difference between the layers nor the design of the color difference between the layers is not considered at all. This is because the foregoing technique has solved the transitivity of the color tones between the layers through the curve design of the boundary surface(s) between the layers. Even in the foregoing technique, because the layer structure involves curved surfaces, various restrictions occur regarding the technical aspect and the cost aspect in the production of the layer structure.

Any of the above-described conventional techniques relates to the color tones and the layer structures of the block materials used in the dental CAD/CAM technique. In these conventional techniques, the color tone of a natural tooth cannot be appropriately reproduced because the technique for color tone design is insufficient, or in order to reproduce the color tone, it is required to produce a block having a complicated layer structure or a layer structure having more than six layers, and accordingly these conventional techniques have a problem of being technically complicated. In particular, when a block material is produced by using as a material a composite resin prepared by mixing a polymerizable monomer and a filler, it is technically extremely difficult to produce a block material having a complicated or continuous layer structure, and the production cost is heightened.

SUMMARY OF THE INVENTION

The present disclosures made a diligent study on the layer structure capable of imparting highly aesthetic features similar to the aesthetic features of a natural tooth to a block material for CAD/CAM using a composite resin as a starting material, and consequently discovered the technique of the present disclosure. Specifically, in a block-shaped material formed of two or more layers different in transparency and color tone from each other, the different transparencies (contrast ratios) of the two or three layers are prescribed so as to meet a certain relationship, and the color tone designs of the respective layers are performed so as to give the color tones relatively approximate to each other. The dental crown prosthetic device obtained by milling and machining of a block having such a design displays the same ivory color and the same enamel color as those of a natural tooth, and at the same time, the interlayer boundary (boundaries) between the layers is not conspicuous.

In the present disclosure, the transparency of a material is represented by the contrast ratio. The contrast ratio is determined from the Y-values obtained by subjecting a 1-mm-thick material to a color measurement over a white background and a black background. Specifically, when the Y-value obtained from the color measurement over the white background is represented by YW and the Y-value obtained from the color measurement on the black background is represented by YB, the contrast ratio is determined on the basis of (contrast ratio)=YB/YW.

In the present disclosure, the color tone of a material is represented on the basis of the L*a*b* colorimetric system. The color tone of a material is represented by the L* value, a* value and b* value obtained by subjecting a material processed so as to have a thickness of 1 mm to a colorimetric measurement over a white background.

The present disclosure provides the following multilayer resin material for dental milling and machining.

(1) A multilayer resin material for dental milling and machining including an inorganic filler in a content of 40% by weight or more and a plurality of layers different in transparency and color tone from each other, wherein the thickness of the uppermost layer (U) and the thickness of the lowermost layer (L) are each 1 mm or more, and the contrast ratios (uppermost layer: $C_U$, lowermost layer: $C_L$) as indices for the transparency of the uppermost layer (U) and the transparency of the lowermost layer (L) satisfy the following relations:

$$0.30 \leq C_U \leq 0.60$$

$$0.55 \leq C_L \leq 0.90$$

$$C_U < C_L$$

and the chromaticities (uppermost layer: $L_U \cdot a_U \cdot b_U$, lowermost layer: $L_L \cdot a_L \cdot b_L$) based on the L*·a*·b* colorimetric system as the indices of the color tones in the uppermost layer (U) and the lowermost layer (L) satisfy the following relations:

$$60 \leq L_U \cdot L_L \leq 80$$

$$-3 \leq a_U \cdot a_L \leq 2$$

$$0 \leq b_U \cdot b_L \leq 30$$

In the present specification, for example, $60 \leq L_U \cdot L_L \leq 80$ shows that $60 \leq L_U \leq 80$ and $60 \leq L_L \leq 80$. Similarly, for example, $-3 \leq a_U \cdot a_L \leq 2$ shows that $-3 \leq a_U \leq 2$ and $-3 \leq a_L \leq 2$.

(2) In the multilayer resin material for dental milling and machining according to foregoing (1), the thickness of a middle layer (M) positioned between the uppermost layer (U) and the lowermost layer (L) is 0.5 mm or more, the contrast ratio ($C_M$) as an index for the transparency in the middle layer (M) preferably satisfies the following relations:

$$0.45 \leq C_M \leq 0.65$$

$$C_U \leq C_M < C_L$$

and the chromaticity (middle layer: $L_M \cdot a_M \cdot b_M$) based on the L*a*b* colorimetric system as the index for the color tone in the middle layer (M) preferably satisfies the following relations:

$$60 \leq L_M \leq 80$$

$$-3 \leq a_M \leq 2$$

$$0 \leq b_M \leq 30$$

In the present specification, in the case where two or more middle layers are present, at least one of the middle layers may satisfy and all the middle layers each more preferably satisfy the foregoing prescription of the thickness, the contrast ratio and the chromaticity.

(3) In the multilayer resin material for dental milling and machining according to foregoing (1) or (2), the contrast ratio difference ($|C_U - C_L|$) between the uppermost layer (U) and the lowermost layer (L) is preferably 0.03 to 0.15.

(4) In the multilayer resin material for dental milling and machining according to foregoing (2), the contrast ratio difference ($|C_U - C_M|$) between the uppermost layer (U) and the middle layer (M) is preferably 0.03 to 0.15, and the contrast ratio difference ($|C_M - C_L|$) between the middle layer (M) and the lowermost layer (L) is preferably 0.03 to 0.15.

In the present specification, in the case where two or more middle layers are present, at least one of the middle layers may satisfy and all the middle layers more preferably satisfy the foregoing prescription of the contrast ratio difference.

(5) In the multilayer resin material for dental milling and machining according to any one of foregoing (1) to (4), the color difference $\Delta E_{UL}$ between the uppermost layer (U) and the lowermost layer (L) is preferably 0.1 to 15.0.

(6) In the multilayer resin material for dental milling and machining according to foregoing (2) or (4), the color difference $\Delta E_{UM}$ between the uppermost layer (U) and the middle layer (M) and the color difference $\Delta E_{ML}$ between the middle layer (M) and the lowermost layer (L) are preferably 0.1 to 15.0.

In the present specification, in the case where two or more middle layers are present, at least one of the middle layers may satisfy and all the middle layers more preferably satisfy the foregoing prescription of the color difference.

(7) In the multilayer resin material for dental milling and machining according to foregoing (1), (3) or (5), the volume ratio between the uppermost layer (U) and the lowermost layer (L) is preferably 1:3 to 1:1.

(8) In the multilayer resin material for dental milling and machining according to foregoing (2), (4) or (6), at least one of the volume ratio between the uppermost layer (U) and the middle layer (M), the volume ratio between the middle layer (M) and the lowermost layer (L) and the volume ratio between the uppermost layer (U) and the lowermost layer (L) is preferably 1:3 to 1:1.

In the present specification, in the case where two or more middle layers are present, at least one of the middle layers may satisfy and all the middle layers more preferably satisfy the foregoing prescription of the volume ratio.

The present disclosure provides the following method for producing a multilayer resin material for dental milling and machining.

(9) A method for producing the multilayer resin material for dental milling and machining according to any one of (1) to (8), produced by stacking uncured paste-like substances in layers and sequentially polymerizing and curing the stacked substances, wherein the difference or differences in the linear polymerization shrinkage rate between the respective layers are 1.0% or less, and/or the difference or differences in the heat generated by polymerization between the respective layers are 50 J/g or less.

According to the resin material for dental milling and machining in the present disclosure, it is possible to prepare dental crown prosthetic devices having high aesthetic quality, even in a layer configuration involving relatively small number of layers such as two or three layers, or in relatively simple shapes, such as planar shapes, of the boundary surfaces between the respective layers.

DETAILED DESCRIPTION OF THE PREFERRED EMBODIMENTS

The resin material for dental milling and machining of the present disclosure include an inorganic filler in a content of 40% by weight or more. The resin material for dental milling and machining of the present disclosure can be obtained, for example, by polymerizing and curing in a die having a desired shape, a paste-like substance prepared by mixing, as the main components, a polymerizable monomer, an inorganic filler, a polymerization catalyst and a colorant. Hereinafter, described are such components capable of being used in the resin material for dental milling and machining of the present disclosure. For the polymerizable monomer as one of the constituent components, heretofore known polymerizable monomers generally used in dental materials can be used without being particularly limited. Examples of the polymerizable monomer include generally radical polymerizable monomers. Examples of the monofunctional polymerizable monomer include: (meth)acrylic acid esters such as methyl (meth)acrylate, ethyl (meth)acrylate, n-butyl (meth)acrylate, isobutyl (meth)acrylate, tert-butyl (meth)acrylate, pentyl (meth)acrylate, isopentyl (meth)acrylate, neopentyl (meth)acrylate, glycidyl (meth) acrylate, tetrahydrofurfuryl (meth) acrylate, 2-hydroxyethyl (meth) acrylate, 2-hydroxypropyl (meth) acrylate, 3-chloro-2-hydroxypropyl (meth) acrylate, ethylene glycol acetoacetate (meth)acrylate, ethylene glycol mono(meth)acrylate, diethylene glycol mono(meth)acrylate, triethylene glycol mono(meth)acrylate, polyethylene glycol mono(meth)acrylate, methoxydiethylene glycol mono(meth)acrylate, methoxytetraethylene glycol (meth) acrylate, methoxypolyethylene glycol (meth) acrylate, β-(meth)acryloxyethyl hydrogen phthalate, β-(meth)acryloxyethyl hydrogen succinate, nonylphenoxyethyl (meth) acrylate, phenoxyethyl (meth) acrylate, phenoxydiethylene (meth)acrylate, N-(2-hydroxy-3-(meth)acryloyloxypropyl)-N-phenylglycine, N-(meth)acryloyl glycine and 4-(meth)acryloyloxyethyl trimellitic acid anhydride; vinyl esters such as vinyl acetate and vinyl propionate; vinyl ethers such as methyl vinyl ether, ethyl vinyl ether, isobutyl vinyl ether and (meth)acrylaldehyde ethyl acetal; alkenylbenzenes such as styrene, vinyltoluene, α-methylstyrene and chlorostyrene; vinyl cyanides such as acrylonitrile and (meth)acrylonitrile; (meth)acrylic acid aldehydes such as (meth)acrylaldehyde and 3-cyano(meth) acrylaldehyde; (meth)acrylic acid amides such as (meth)acrylamide, N-succin(meth)acrylamide and N,N-dimethylmethacrylamide; polymerizable monomers containing an unsaturated carboxylic acid group such as (meth)acrylic acid, vinylacetic acid and crotonic acid, or the metal salts of these; polymerizable monomers containing a phosphoric acid ester group such as acid phosphoethyl (meth)acrylate, acid phosphopropyl (meth)acrylate and 2-(meth)acryloyloxyethylphenyl phosphate, or the metal salts of these; polymerizable monomers containing a sulfonic acid group such as allylsulfonic acid, (meth)acrylsulfonic acid, styrenesulfonic acid and tert-butyl(meth)acrylamide sulfonic acid, or the metal salts of these.

Examples of the bifunctional polymerizable monomer include: diol di(meth)acrylates such as ethylene diol di(meth)acrylate, propylene diol di(meth)acrylate, propane diol di(meth)acrylate, butane diol di(meth)acrylate, hexane diol di(meth)acrylate, octane diol di(meth)acrylate, nonane diol di(meth)acrylate, decane diol di(meth)acrylate and eicosane diol di(meth)acrylate; glycol di(meth)acrylates such as ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butylene glycol di(meth)acrylate and neopentyl glycol di(meth)acrylate; urethane-based polymerizable monomers derived from adducts between vinyl monomers having a vinyl group such as 2-hydroxyethyl (meth)acrylate, 2-hydroxypropyl (meth) acrylate and 3-chloro-2-hydroxypropyl (meth)acrylate and diisocyanate compounds such as hexamethylene diisocyanate, trimethylhexamethylene diisocyanate, diisocyanate methylcyclohexane, isophorone diisocyanate and methylbis (4-cyclohexylisocyanate); (meth)acrylate-based polymerizable monomers having an aromatic ring(s) and a urethane bond(s) derived from the adducts between vinyl monomers having a hydroxyl group such as 2-hydroxyethyl (meth) acrylate, 2-hydroxypropyl (meth)acrylate and 3-chloro-2-hydroxypropyl (meth)acrylate and aromatic ring-containing diisocyanate compounds such as diisocyanate methylbenzene and 4,4'-diphenylmethane diisocyanate; (meth)acrylate-based polymerizable monomers having an aromatic ring(s) and an ether bond(s) such as 2,2-bis((meth)acryloxyphenyl)propane, 2,2-bis[4-(3-(meth)axcryloxy)-2-hydroxypropoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypolyethoxyphenyl)propane, 2,2-bis(4-(meth)acryloxydipropoxyphenyl)propane, 2-(4-(meth)acryloxyethoxy phenyl)-2-(4-(meth)acryloxyphenyl)propane, 2-(4-(meth)acryloxydiethoxy phenyl)-2-(4-(meth)acryloxytriethoxy phenyl)propane, 2-(4-(meth)acryloxydipropoxyphenyl)-2-(4-(meth)acryloxytriethoxyphenyl)propane and 2,2-bis(4-(meth)acryloxyisopropoxyphenyl)propane; and 1:2 reaction product between bisphenol A or hydrogenated bisphenol A and glycidyl (meth)acrylate such as 1:2 adduct between bisphenol A or hydrogenated bisphenol A and epoxy group-containing (meth)acrylate such as bisphenol A diglycidyl ether (meth)acrylic acid adduct.

Examples of the polyfunctional polymerizable monomer having three or more polymerizable functional groups include: tri(meth)acrylates and tetra(meth)acrylates such as trimethylolmethane tri(meth)acrylate, trimethylolethane tri (meth)acrylate, trimethylolpropane tri(meth)acrylate, pentaerythritol tetra(meth)acrylate, tri(meth)acrylate having a phosphazene skeleton, tri(meth)acrylate having an isocyanuric acid skeleton, pentaerythritol tetra(meth)acrylate and ditrimethylolpropane tetra(meth)acrylate; urethane-based polymerizable monomers derived from diisocyanate compounds such as diisocyanate methylbenzene, 4,4'-diphenylmethane diisocyanate, hexamethylene diisocyanate, trimethylhexamethylene diisocyanate, diisocyanate methylcyclohexane, isophorone diisocyanate, methyl bis(4-cyclohexyl isocyanate) and vinyl monomers having a hydroxyl group such as glycidol dimethacrylate; polymerizable monomers having five or more, ethylenically unsaturated groups such as dipentaerythritol hydroxy penta(meth) acrylate; polymerizable multifunctional acrylates including polyethylenically unsaturated carbamoyl isocyanurate; polymerizable multifunctional acrylates having a urethane bond such as phenyl glycidyl ether acrylate hexamethylene diisocyanate urethane prepolymer, phenyl glycidyl ether toluene diisocyanate urethane prepolymer, pentaerythritol triacrylate toluene diisocyanate urethane prepoilymer and pentaerythritol triacrylate isophorone diisocyanate urethane prepolymer; ditrimethylolpropane tetraacrylate, ethoxylated pentaerythritol tetraacrylate, propoxylated pentaerythritol tetraacrylate, pentaerythritol tetra(meth)acrylate, dipentaerythritol tetra(meth)acrylate, dipentaerythritol penta(meth)acrylate, dipentaerythritol hexa(meth)acrylate and trimethylpropane tri(meth)acrylate.

In the present disclosure, the foregoing polymerizable monomers can be mixed each alone or as mixtures of two or more thereof. By mixing two or more polymerizable monomers, the refractive indices and the physical properties of the polymerizable monomers can be regulated. The mixing amount of the polymerizable monomer(s) is preferably 5% by weight or more and less than 60% by weight in the resin material for dental milling and machining of the present disclosure. The mixing amount of the polymerizable monomer(s) is further preferably 10% by weight or more and less than 50% by weight. When the mixing amount of the polymerizable monomer(s) is too small, it comes to be difficult to prepare a paste-like substance by mixing the polymerizable monomer(s) and the inorganic filler. The upper limit of the polymerizable monomer(s) is determined by the mixing amount of the inorganic filler.

For the inorganic filler as a constituent component of the present disclosure, heretofore known inorganic fillers used for dental materials can be used without being particularly limited. Examples of the material of the inorganic filler include: kaolin, talc, quartz, silica, colloidal silica, alumina, aluminosilicate, silicon nitride, barium sulfate, calcium phosphate, various glasses (such as fluoro-glass, borosilicate glass, soda glass, barium glass, glass containing strontium or zirconium, glass ceramics, fluoroaluminosilicate glass and synthetic glass by sol-gel method), zirconia, zirconium silicate and hydroxy apatite. The shape, the particle size distribution, the average particle size and the like of the inorganic filler are not particularly limited. However, similarly to the common dental resin material (such as composite resin) with an inorganic filler mixed therein, while the material strength is being enhanced, the material strength and the surface lubricity are required to be made compatible with each other. Accordingly, the average particle size is desired to be 50 μm or less, preferably 10 μm or less, and further preferably 1 μm or less.

The inorganic filler used in the present disclosure is preferably subjected to surface treatment. Examples of the surface treatment material include: silane compounds such as vinyltrimethoxysilane, vinyltriethoxysilane, vinyltrichlorosilane, vinyltri(β-methoxyethoxy)silane, γ-methacryloxypropyltrimethoxysilane, γ-glycidoxypropyltrimethoxysilane, γ-mercaptopropyltrimethoxysilane and γ-aminopropyltriethoxysilane.

The inorganic filler as a constituent component of the present disclosure is subject to a requirement that the filler is included in the multilayer resin material for dental milling and machining in a content of 40% by weight or more. The prosthetic device obtained by milling and machining the multilayer resin material for dental milling and machining according to the present disclosure is basically intended to function over a long term (2 years or more) in the oral cavity. Accordingly, the prosthetic device is required to have durability under the high temperature and the high humidity specific to the inside of the oral cavity, and is required to be reinforced with a certain amount or more of an inorganic filler. When the mixing proportion of the inorganic filler is less than 40% by weight, it is difficult to allow the prosthetic device or the like based on the multilayer resin material for dental milling and machining of the present disclosure to stably function over a long term in the oral cavity. The material of the present disclosure is desired to mix an inorganic filler in a mixing proportion of preferably 50% by weight or more, and further preferably 60% by weight or more.

For the polymerization catalyst as a constituent component of the present disclosure, heretofore known polymerization catalyst used for dental materials can be used without being particularly limited. Examples of the photopolymerization catalyst include: benzophenone, diacetyl, benzil, 4,4'-dimethoxybenzil, 4,4'-oxybenzil, 4,4'-dichlorobenzil, camphorquinone, camphorquinone carboxylic acid, 2,3-pentadione, 2,3-octadione, 9,10-phenanthrenequinone, acenaphthenequinone, 2,4,6-trimethylbenzoyl diphenyl phosphine oxide, 2,6-dimethylbenzoyl diphenyl phosphine oxide, 2,6-dimethoxybenzoyl diphenyl phosphine oxide, 2,6-dichlorobenzoyl diphenyl phosphine oxide, 2,3,5,6-tetramethylbenzoyil diphenyl phosphine oxide, methyl 2,4,6-trimethylbenzoyl phenylphosphinate, ethyl 2,4,6-trimethylbenzoyl phenylphosphinate ethyl and phenyl 2,4,6-trimethylbenzoyl phenylphosphinate.

For example, as a thermal (chemical) polymerization catalyst, the following are effective: diacyl peroxides, peroxy esters, dialkyl peroxides, peroxyketals, ketone peroxides and hydroperoxides. Specific examples of the foregoing diacyl peroxides include benzoylperoxide, 2,4-dichlorobenzoylperoxide and m-toluoyl peroxide.

In combination with the foregoing polymerization catalysts, heretofore known polymerization promoters may also be used without being limited. Examples of such a polymerization promoter include: N,N-dimethylaniline, N,N-diethylaniline, N,N-dibenzylaniline, N,N-dimethyl-p-toluidine, N,N-diethyl-p-toluidine, N,N-dihydroxyethyl-p-toluidine, N,N-dimethylaminobenzoic acid, N,N-diethylaminobenzoic acid, ethyl N,N-dimethylaminobenzoate, ethyl N,N-diethylaminobenzoate, methyl N,N-dimethylaminobenzoate, methyl N,N-diethylaminobenzoate, N,N-dimethylaminobenzaldehyde, N,N-dihydroxyethylaniline, p-dimethylaminophenetyl alcohol, N,N-dimethylaminoethyl methacrylate, N,N-dimethylaminoethyl methacrylate, triethylamine, tributylamine, tripropylamine and N-ethylethanolamine.

The mixing amount of the foregoing polymerization catalyst is, in relation to 100 parts by weight of the polymerizable monomer, 0.01 to 5 parts by weight, more preferably 0.05 to 3 parts by weight and further preferably 0.1 to 2 parts by weight. When the mixing amount of the polymerization catalyst is too small, an insufficient polymerization of the polymerizable monomer occurs. In contrast, when the mixing amount of the polymerization catalyst is too large, the termination reaction during polymerization is accelerated and consequently the strength degradation of the material is caused.

The mixing of a chain transfer agent in the polymerizable monomer allows the resin material for dental milling and machining of the present disclosure to be uniformly polymerized and cured. For the chain transfer agent, heretofore known compounds can be used without being limited. Specific examples of the chain transfer agent include: mercaptan compounds such as n-butylmercaptan and n-octylmercaptan; terpenoid-based compounds such as limonene, myrcene, α-terpinene, β-terpinene, γ-terpinene, terpinolene, β-pinene and α-pinene; and α-methylstyrene dimer. Among these chain transfer agents, the terpenoid-based compounds are particularly preferable. Specifically, α-terpinene, β-terpinene and γ-terpinene are particularly preferable.

The mixing amount of the chain transfer agent is, in relation to 100 parts by weight of the polymerizable monomer, preferably 0.001 to 1 part by weight and further preferably 0.1 part by weight or more and 0.5 part by weight or less.

In the resin material for dental milling and machining of the present disclosure, for the colorant as a constituent component, the heretofore known colorants used in the dental materials are used without being limited. As the colorants, either an inorganic compound-based colorant or an organic compound-based colorant can be used. In particular, a white colorant is useful for the regulation of the transparency of each of the layers of the present disclosure.

In the resin material for dental milling and machining of the present disclosure, a heretofore known organic filler can be mixed if necessary. Examples of the organic filler include: polymethylmethacrylate (PMMA), polyethylmethacrylate, polypropylmethacrylate, polybutylmethacrylate, polyvinyl acetate, polyethyleneglycol, polypropyleneglycol and polyvinyl alcohol. In addition, examples of an organic composite filler include: a filler prepared by covering the surface of an inorganic filler with a polymerixzable monomer through polymerization, and by subsequently crushing the thus treated inorganic filler so as to have an appropriate particle size, or a filler prepared as particles by beforehand mixing an inorganic filler in a polymerizable monomer, subsequently polymerizing the polymerizable monomer, and successively crushing the thus treated inorganic filler.

In the resin material for dental milling and machining of the present disclosure, heretofore known various additives can be mixed if necessary. Examples of such additives include a polymerization inhibitor, a discoloration preventing agent, a fluorescent agent, an ultraviolet absorber and an antibacterial agent.

The resin material for dental milling and machining of the present disclosure can be a block-like material to be used in a dental CAD/CAM system. A common block-like material has an edge length of approximately 10 to 20 mm, and this is assumed to correspond to the dental crown length of a natural tooth of 5 to 15 mm. In the present disclosure, an edge extending from the uppermost layer to the lowermost layer is assumed to adapt to the dental crown lengthwise direction usually set to be 10 to 20 mm.

On the basis of the premise that an edge extending from the uppermost layer (U) to the lowermost layer (L) in the resin material for dental milling and machining of the present disclosure adapts to the dental crown lengthwise direction, the layer structure extending from the uppermost layer (U) to the lowermost layer (L) can be assumed as the layer structure extending from the dental crown tip to the dental crown root. On the other hand, in a natural tooth, the tip thereof is structurally constituted only with an enamel and exhibits an enamel color, and the enamel gets thinner toward the root, and the ivory color is correspondingly enhanced. Accordingly, in the resin material for dental milling and machining of the present disclosure, the uppermost layer (U) is designed so as to have an enamel color and the lowermost layer (L) is designed so as to have an ivory color; however, here is caused a problem such that the layer structure imparted to such a block body as in the present disclosure is not consistent with the layer structure of a natural tooth including the enamel and the dentin.

In the foregoing conventional techniques, an effort has been achieved a in such a way that curved surfaces are imparted to a block body so as for the block body to have a layer structure as similar as possible to the layer structure of a natural tooth, or an effort has also been achieved in such a way that the number of the layers is increased so as to finely vary the color tone of each of the layers. However, the impartment of curved surfaces to the layer structure or the increase of the number of the layers is unpractical because of imposing a large burden in view of the technical aspect or the cost aspect of the production. In the present disclosure, even in the case where the layer structure of the block body is constituted with relatively simple planar layers, or even in a case where the number of the layers is as small as two or three, the transition of the color tone of each of the layers is intended to look smooth. Specifically, this is a technique allowing the color tone variation as the whole of the block to be visually perceived smoothly, by designing the transparency and the color tone of each layer as prescribed in detail. In the present disclosure, a prosthetic device having a color tone similar to the color tone of a natural tooth is obtained in spite of a relatively simple layer structure of the block body, by milling and machining the block body, on the basis of the design such that the contrast ratio and the color tone of the uppermost layer (U) are designed so as to be adaptable to the enamel color, the contrast ratio and the color tone of the lowermost layer (L) are designed so as to be adaptable to the ivory color, further the color tone of the uppermost layer (U) and the color tone of the lowermost layer (L) are designed so as to be similar to each other, and the uppermost layer (U) is designed so as to be disposed on the dental crown tip side and the lowermost layer (L) is designed so as to be disposed on the dental crown root side.

In practical clinic, from the resin material for dental milling and machining, dental crown prosthetic devices having various forms and sizes are prepared. Accordingly, it is difficult to uniformly set the layer configuration and the thickness of each of the layers in the block-like materials supplied for the purpose of preparing the dental crown prosthetic devices. However, in the prosthetic device after machining, the thickness of each of the layers is considered to be required to be 1 mm or more as the layer thickness allowing the color tone of a portion to be definitely visible. On the basis of this consideration, the thickness of the uppermost layer (U) and the thickness of the lowermost layer (L) in the resin material for dental milling and machining of the present disclosure are set to be 1 mm or more. In consideration of the application to a natural tooth of an adult, the thickness of the uppermost layer (U) and the thickness of the lowermost layer (L) are considered to be set to be preferably 2 mm or more.

In the case where the middle layer (M) is set between the uppermost layer (U) and the lowermost layer (L), the middle layer (M) plays a role for allowing the variation of the contrast ratio/color tone to be further transitional. Accordingly, the contrast ratio and the color tone of the middle layer (M) are not required to be set independently, and when the thickness of the middle layer (M) is at least 0.5 mm, the role as the middle layer (M) is achieved.

As described above, it is difficult to uniformly set the layer configuration and the thickness of each of the layers of the block-like material; however, it is preferable to set the volume ratio between the uppermost layer (U) assumed to have the enamel color and the lowermost layer (L) assumed to have the ivory color to be 1:3 to 1:1 in imitation of the structure of a natural tooth. When the volume ratio between the uppermost layer (U) and the lowermost layer (L) deviates from 1:3 to 1:1, the enamel color of the prosthetic device after the machining may be extremely faded, and conversely, the ivory color may be extremely faded, and thus the effect of definitely visually perceiving the respective layers may not be obtained sometimes. Accordingly, the color tone of the prosthetic device comes to be monotonous, and may be unnatural sometimes as compared with a natural tooth. In the case where the middle layer (M) is set between the uppermost layer (U) and the lowermost layer (L), the volume ratio between the uppermost layer (U) and the lowermost layer (L) is preferably set to be 1:3 to 1:1, and the volume ratio between the middle layer (M) and the lowermost layer (L) is preferably set to be 1:3 to 1:1. When the volume ratio between the uppermost layer (U) and the middle layer (M) deviates from 1:3 to 1:1, or when the volume ratio between the middle layer (M) and the lowermost layer (L) deviates from 1:3 to 1:1, the enamel color of the prosthetic device after the machining may be extremely faded, and conversely, the ivory color may be extremely faded, and thus the effect of definitely visually perceiving the respective layers may not be obtained sometimes. Accordingly, the color tone of the prosthetic device comes to be monotonous, and may be unnatural sometimes as compared with a natural tooth.

In the case of the dental material such as a porcelain material or a hard resin material, dental crown prosthetic devices have hitherto been prepared by laminating a plurality of materials different in transparency and color tone from each other such as an ivory color layer and an enamel color layer. Owing to many years of research, the transparency (contrast ratio) of the material reproducing the ivory color and the transparency (contrast ratio) of the material reproducing the enamel color have been investigated. In the present disclosure, from the knowledge of conventional techniques and a result of a diligent study of the color tone reproducibility in the case where the dental crown prosthetic device is machined from a block-like material, the contrast ratio $C_U$ of the uppermost layer (U) assumed to have the enamel color is set at 0.30 to 0.60. The further preferable range of the contrast ratio $C_U$ of the uppermost layer (U) is 0.35 to 0.52. The contrast ratio $C_L$ of the lowermost layer (L) assumed to have the ivory color is set at 0.55 to 0.90. The further preferable range of the contrast ratio $C_L$ of the lowermost layer (L) is 0.58 to 0.85. Moreover, the relationship between the contrast ratio $C_U$ of the uppermost layer (U) and the contrast ratio of $C_L$ of the lowermost layer (L) is set to satisfy $C_U < C_L$. In the case where the middle layer (M) is set, the contrast ratio ($C_M$) is set to be 0.45 to 0.65. The further preferable range of the contrast ratio ($C_M$) of the middle layer (M) is 0.50 to 0.60. Moreover, the relationship between the contrast ratio $C_U$ of the uppermost layer (U) and the contrast ratio $C_L$ of the lowermost layer (L) is set to satisfy $C_U < C_M < C_L$.

The uppermost layer (U) and the lowermost layer (L) (and the middle layer (M)) in the resin material for dental milling and machining of the present disclosure are required to be designed so as to be different in transparency from each other. The contrast ratio differences between the respective layers ($|C_U - C_L|$) (and ($|C_U - C_M|$) and ($|C_M - C_L|$)) are at least 0.03, and preferably 0.05. Herewith, the differences between the respective layers come to be definitely recognizable. When the respective layers are largely different in transparency from each other, the color tone of the prepared prosthetic device comes to be unnatural. Accordingly, the contrast ratio differences between the respective layers ($|C_U - C_L|$) (and ($|C_U - C_M|$) and ($|C_M - C_L|$)) are required to be designed so as not to exceed 0.15 and preferably 0.12.

In the present disclosure, the transparency (contrast ratio) of each of the layers is required to be varied. The methods for regulating the transparency of a material in an inorganic filler-containing resin material (composite material) are roughly classified into two methods. One method is a method for regulating the refractive index difference between the polymerizable monomer and the inorganic filler. When the refractive index difference between these two substances is small, the transparency of the material is increased, and on the contrary when the refractive index difference is large, the transparency of the material is decreased. Another method for regulating the transparency of a material is a method for regulating the mixing amount of an opaque colorant (white colorant). In the implementation of the method for producing the multilayer resin material for dental milling and machining of the present disclosure, in particular in the case of adopting a technique of simultaneously and uniformly polymerizing the materials of a plurality of layers different in color tone from each other, the respective layers preferably allow the same polymerization reaction to proceed. Accordingly, the condition that the type of the polymerizable monomer and the type of the inorganic filler are different for each of the layers requires attention because there is a possibility that the reaction progress is different for each of the layers. A method in which the types of the polymerizable monomers and the types of the inorganic fillers of the respective layers are set to be the same as each other, and the transparency of each of the layers is varied by mixing a trace amount of an opaque colorant (white colorant) allows the polymerization reactions of the respective layers to proceed uniformly. However, even in the case of the method adopting the addition of an opaque colorant, when the material is cured by photopolymerization, further attention is required. When a block body is molded by photopolymerization, it is preferable to mold the block body by repeating, for each of the layers, the polymerization and the filling.

The present disclosure is characterized in that the color tones of the uppermost layer (U) and the lowermost layer (L) (and the middle layer (M)) are approximated to each other. When the dental crown prosthetic device milled and machined from the material of the present disclosure is observed, the respective layers are recognized as the enamel part and the ivory part (and the middle part) because the respective layers are different in transparency (contrast ratio) from each other, and moreover, the color tones of the respective layers are approximated to each other, and hence it is difficult to perceive the boundaries between the respective layers. In the present disclosure, the design of the color tone of each of the layers is such that the range capable of functioning as either color tone of the enamel color and the ivory color is set by referring to the color tone design implemented for conventional porcelain materials or hard resin materials. Specifically, in the L*a*b* colorimetric system, $60 \leq L^* \leq 80$, $-3 \leq a^* \leq 2$ and $0 \leq b^* \leq 30$. Further preferably, $65 \leq L^* \leq 75$, $-2.5 \leq a^* \leq 0.5$ and $5 \leq b^* \leq 20$.

In the present disclosure, the color differences between the respective layers, namely, the uppermost layer (U) and the lowermost layer (L) (and the middle layer (M)) is preferably 0.1 to 15.0 in terms of ΔE. Further preferably, ΔE is 0.1 to 12.0. Herewith, the transition of the color tone in the respective layers looks smooth, and a prosthetic device similar to a natural tooth can be obtained. Here, in the present specification, the color difference $\Delta E_{UL}$ between the uppermost layer (U) and the lowermost layer (L) is defined by $\Delta E_{UL} = ((L_U - L_L)^2 + (a_U - a_L)^2 + (b_U - b_L)^2)^{0.5}$. Similarly, the color difference $\Delta E_{UM}$ between the uppermost layer (U) and the middle layer (M) is defined by $\Delta E_{UM} = ((L_U - L_M)^2 + (a_U - a_M)^2 + (b_U - b_M)^2)^{0.5}$. In addition, the color difference $\Delta E_{ML}$ between the middle layer (M) and the lowermost layer (L) is defined by $\Delta E_{ML} = ((L_M - L_L)^2 + (a_M - a_L)^2 + (b_M - b_L)^2)^{0.5}$.

In the implementation of the present disclosure, the production method thereof is not particularly limited. A paste prepared by mixing a polymerizable monomer, an inorganic filler, a polymerization catalyst, a colorant and the like is filled in a die and the paste is polymerized and cured. For the impartment of the layer structure, for example, there are a method in which one layer is filled in a die and polymerized, and then the next layer is filled in another die and polymerized, and another method in which the pastes of the respective layers colored in different color tones are sequentially filled in a die, and then are collectively polymerized. According to these production methods, the dies are appropriately designed. Specifically, in the case where the filling and polymerization are repeated for each layer, a plurality of sets of dies designed according to the structures of the respective layers are prepared. In the case where the plurality of layers are collectively polymerized, a die designed according to the shape of the whole of the block body is prepared. In the case where the polymerization and curing are performed by photopolymerization, the die is required to be made from a material having optical transparency such as a resin or silicon.

In the implementation of the method for producing the multilayer resin material for dental milling and machining of the present disclosure, in particular, in the case where a plurality of layers are simultaneously polymerized and cured, it is important that the polymerization reactions of the materials constituting the respective layers are allowed to proceed evenly. In the present disclosure, as the polymerizable monomers of the constituent elements, the use of polymerizable monomers having radical polymerization property is assumed, and these polymerizable monomers undergo approximately a few percent to 20% of polymerization shrinkage during polymerization. If the types of the polymerizable monomers used in the respective layers are different from each other, or the mixing amounts of the inorganic filler(s) in the respective layers are different from each other, the polymerization shrinkage rates in the respective layers are different from each other. When the polymerization shrinkage rates of the respective layers are largely different from each other, distortions are caused between the respective layers after the polymerization. When the distortions are large, breakage may be sometimes caused in the block body in the course of the production. Even when a multilayer block body has been successfully produced, the residual stress is caused inside the block body, and hence the durability of the block body may be sometimes degraded. Accordingly, the polymerization shrinkage rates of the respective layers are required to be as close to each other as possible. The polymerization shrinkage rate differences between the uncured paste-like substances constituting the respective layers are preferably 1.0% or less in terms of the linear polymerization shrinkage rate. The foregoing differences are further preferably 0.6% or less.

From the viewpoint of avoiding the occurrence of the residual stress inside the block body, the amount of the heat generated by the polymerization reaction offers a significant factor. The polymerization heat generation affects the polymerization rate of the material, the thermal expansion (shrinkage) of the material and the like. If the heats generated by polymerization in the respective layers are different from each other, the resulting polymerization rates of the respective layers are different from each other to cause inter-layer distortions during polymerization. Also, when an external stress is exerted on the block body after production, distortion stresses are generated between the layers due to the different moduli of elasticity of the respective layers. Moreover, the temperature of the block body is heightened due to the heat generated by polymerization during the polymerization reaction, but the block body is cooled after completion of the reaction. In this case, the thermal shrinkage of each of the materials is caused, and when the heats generated by polymerization of the respective layers are different from each other, naturally the thermal shrinkage magnitudes of the respective layers are different from each other. In other words, the heats generated by polymerization offer the factors to cause distortions between the layers. Accordingly, the heats generated by polymerization of the components constituting the respective layers are required to be made as close to each other as possible. The differences between the heats generated by polymerization of the uncured paste-like substances constituting the respective layers are preferably 50 J/g or less, and further preferably 10 J/g or less.

EXAMPLES

Hereinafter, the present disclosure is described by way of Examples in more detail, and specifically, but the present disclosure is not limited to these Examples.

(Measurement of Chromaticity and Contrast Ratio)

The uncured paste-like substances to be used for the respective layers of each Example were filled in a ϕ15 mm×1.2 mm die, polymerized and cured. The disk-like product after molding was regulated so as to have a thickness of 1.0 mm with water-resistant polishing paper, and the surface of the disk-like product was finish-polished by buffing. The disk-like product after polishing was subjected to the measurement of the L*a*b* value over a white background by using a spectrocolorimeter (CM-3500d: Konica Minolta). The same measurement was performed over a black background, and from the Y value (YW) of white background colorimetry and the Y value (YB) of black background colorimetry, YB/YW was defined as the contrast ratio.

(Linear Shrinkage Rate)

The uncured paste-like substances to be used for the respective layers of each Example were filled in a 12×14×18 mm die for preparation of a block body, polymerized and cured. The dimension of the 12-mm edge of the die and the dimension of the 12-mm edge of the block body after polymerization and curing were accurately measured, and the linear polymerization shrinkage rate of the paste-like substance was derived from (die dimension−block dimension)/die dimension×100.

(Heat Generated by Polymerization)

The uncured paste-like substances to be used for the respective layers of each Example were analyzed with a differential scanning calorimeter (DSC), and the heat generated by polymerization was measured.

(Evaluation of Color Tone of Prosthetic Device)

A molded block body was milled and machined by using a dental CAD/CAM milling and machining machine DWX-50 (Roland) to prepare a crown for a right first premolar of lower jaw. The prepared crown was visually observed by 10 persons, and the evaluation of the color tone reproducibility (reproducibility of enamel color and ivory color) and the evaluation of the boundaries between the layers as a dental crown prosthetic device were combined, and thus, the evaluation of the color tone of the prosthetic device was performed. In Table 1 and Table 2, the evaluation in the column of "color tone of prosthetic device" are as follows: the case where 10 visual observers in the 10 visual observers gave the evaluation that the color tone reproducibility was satisfactory and the boundaries between the layers was not able to be identified is represented by "AA: the color tones is perfectly reproduced"; the case where nine observers gave the foregoing evaluation is represented by "A: the color tone reproducibility is extremely satisfactory"; the case where eight or seven observers gave the foregoing evaluation is represented by "B: the color tone reproducibility is good"; and the case where six or less observers gave the foregoing evaluation is represented by "C: the color reproducibility is poor."

(Evaluation of Breakage and Cracks during Molding Block Body)

The exterior appearance of a molded block body was visually examined, and the evaluation of the breakage and the cracks was performed. In Table 1, the column of the evaluation of "breakage and cracks of block body during molding" is represented as follows: the case where neither breakage nor cracks were found is represented by "A (no occurrence)"; the case where the occurrence rate of breakage and cracks was less than 5% is represented by "B (occurrence in small amount)"; the case where the occurrence rate of breakage and cracks was 5% or more is represented by "C (occurrence in large amount)." As shown in the table, the occurrence of breakage and cracks in a rate of 5% or more was not identified in any of Examples and Comparative Examples.

(Durability under High Temperature and High Humidity)

The foregoing prepared crown was allowed to stand under the conditions that the crown was placed in water at a temperature of 37° C., as a compulsory test assuming the inside of the oral cavity under high temperature and high humidity, and the durability under high temperature and high humidity was evaluated on the basis of whether or not the color tone stability as a crown was impaired. In Table 1, in the column of the evaluation of the "durability under high temperature and high humidity," the case where the color tone stability as a crown was not impaired in any crown is represented by "A (satisfactory)" and the case where the color tone stability was impaired in a part of the crowns was represented by "B (occurrence)."

(Preparation of Pastes P-1 to 11, 19 to 43, 47 to 51)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.3 part by weight of benzoyl peroxide: BPO. To 40 parts by weight of the polymerizable monomer liquid mixture, 60 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance. By varying the mixing amounts of the respective colorants, 44 types (P-1 to 11, 19 to 43, and 47 to 51) of paste-like substances each having a desired transparency and a desired color tone were prepared.

(Preparation of Pastes P-12 to 14)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.1 part by weight of benzoyl peroxide: BPO. To 20 parts by weight of the polymerizable monomer liquid mixture, 80 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance. By varying the mixing amounts of the respective colorants, 3 types (P-12 to 14) of paste-like substances each having a desired transparency and a desired color tone were prepared.

(Preparation of Pastes P-15 and 16)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.3 part by weight of benzoyl peroxide: BPO. To 60 parts by weight of the polymerizable monomer liquid mixture, 40 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance. By varying the mixing amounts of the respective colorants, 2 types (P-15 and 16) of paste-like substances each having a desired transparency and a desired color tone were prepared.

(Preparation of Pastes P-17 and 18)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.3 part by weight of benzoyl peroxide: BPO. To 65 parts by weight of the polymerizable monomer liquid mixture, 35 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance. By varying the mixing amounts of the respective colorants, 2 types (P-17 and 18) of paste-like substances each having a desired transparency and a desired color tone were prepared.

(Preparation of Paste P-44)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.2 part by weight of benzoyl peroxide: BPO. To 40 parts by weight of the polymerizable monomer liquid mixture, 60 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance (P-44).

(Preparation of Paste P-45) There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.1 part by weight of benzoyl peroxide: BPO. To 40 parts by weight of the polymerizable monomer liquid mixture, 60 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance (P-45).

(Preparation of Paste P-46)

There was prepared a polymerizable monomer liquid mixture including 70 parts by weight of 1,6-bis-methacrylethyl-oxycarbonylamino(2,2,4-)trimethylhexane: UDMA, 30 parts by weight of triethylene glycol dimethacrylate: 3G and 0.05 part by weight of benzoyl peroxide: BPO. To 40 parts by weight of the polymerizable monomer liquid mixture, 60 parts by weight of a mixed filler composed of a silica filler and a zirconium silicate filler was added, and a white colorant, a red colorant, a yellow colorant and a black colorant (the total amount of these colorants was less than 1 part by weight in relation to 100 parts by weight of the mixture of the polymerizable monomer liquid mixture and the mixed filler) were each added in a trace amount to the resulting mixture, and the obtained mixture was kneaded to prepare a paste-like substance (P-46). [0072]

Examples 1 to 6, Examples 8 to 25, Examples 30 to 33, Comparative Examples 1 and 2, and Comparative Examples 4 to 13

In a 12×14×18 mm die for preparing a block body, a paste-like substance for the lowermost layer was filled up to a height of 8 mm in relation to the height of the 12-mm edge. Successively, on the top of the filled paste-like substance for the lowermost layer, a paste-like substance for the uppermost layer was filled (the height of the uppermost layer: 4 mm). The die was heated to 100° C., the paste-like substances were polymerized and cured to yield a block body having a two-layer structure. By using the paste-like substances varied in transparency and color tone, Examples 1 to 6, Examples 8 to 25, Examples 30 to 33, Comparative Examples 1 and 2 and Comparative Examples 4 to 13 shown in Table 1 were prepared. Tables 1 to 5 describe the paste numbers of the paste-like substances used, together with the measured chromaticities and the measured contrast ratios.

Example 7

In a 12×14×18 mm die for preparing a block body, a paste-like substance for the lowermost layer was filled up to a height of 3 mm in relation to the height of the 12-mm edge. Successively, on the top of the filled paste-like substance for the lowermost layer, a paste-like substance for the uppermost layer was filled (the height of the uppermost layer: 9 mm). The die was heated to 100° C., the paste-like substances were polymerized and cured to yield a block body having a two-layer structure. By using the paste-like substances varied in transparency and color tone, Example 7 shown in Table 1 was prepared. Table 1 describes the paste number of the paste-like substance used, together with the measured chromaticity and the measured contrast ratio.

Examples 26 to 29

In a 12×14×18 mm die for preparing a block body, a paste-like substance for the lowermost layer was filled up to heights of 9.6 mm, 9 mm, 6 mm and 4 mm in Examples 26 to 29, respectively, in relation to the height of the 12-mm edge. Successively, on the top of the filled paste-like substance for the lowermost layer, a paste-like substance for the uppermost layer was filled (the heights of the uppermost layers were 2.4 mm, 3 mm, 6 mm and 8 mm in Examples 26 to 29, respectively). The die was heated to 100° C., the paste-like substances were polymerized and cured to yield block bodies having a two-layer structure. By using the paste-like substances varied in transparency and color tone, Examples 26 to 29 shown in Table 5 were prepared. Table 5 describes the paste numbers of the paste-like substances used, together with the measured chromaticities and the measured contrast ratios.

Comparative Example 3

In a 12×14×18 mm die for preparing a block body, a paste-like substance for the lowermost layer was filled up to a height of 11.2 mm in relation to the height of the 12-mm edge. Successively, on the top of the filled paste-like substance for the lowermost layer, a paste-like substance for the uppermost layer was filled (the height of the uppermost layer: 0.8 mm). The die was heated to 100° C., the paste-like substances were polymerized and cured to yield a block body having a two-layer structure. By using the paste-like substances varied in transparency and color tone, Comparative Example 3 shown in Table 1 was prepared. Table 1 describes the paste number of the paste-like substance used, together with the measured chromaticity and the measured contrast ratio.

Examples 34 to 40

In a 12×14×18 mm die for preparing a block body, a paste-like substance for the lowermost layer was filled up to a height of 6 mm in relation to the height of the 12-mm edge. Successively, on the top of the filled paste-like substance for the lowermost layer, a paste-like substance for the middle layer was filled (the height of the middle layer: 3 mm). Moreover, on the top of the filled paste-like substance for the middle layer, a paste-like substance for the uppermost layer was filled (the height of the uppermost layer: 3 mm). The die was heated to 100° C., the paste-like substances were polymerized and cured to yield block bodies having a three-layer structure. By using the paste-like substances varied in transparency and color tone, Examples 34 to 40 shown in Table 6 were prepared. Table 6 describes the paste numbers of the paste-like substances used, together with the measured chromaticities and the measured contrast ratios.

Example 41

In a 12×14×18 mm die for preparing a block body, a paste-like substance for the lowermost layer was filled up to a height of 2 mm in relation to the height of the 12-mm edge. Successively, on the top of the filled paste-like substance for the lowermost layer, a paste-like substance for the middle layer was filled (the height of the middle layer: 4 mm). Moreover, on the top of the filled paste-like substance for the middle layer, a paste-like substance for the uppermost layer was filled (the height of the uppermost layer: 6 mm). The die was heated to 100° C., the paste-like substances were polymerized and cured to yield a block body having a three-layer structure. By using the paste-like substances varied in transparency and color tone, Example 41 shown in Table 6 was prepared. Table 6 describes the paste number of the paste-like substance used, together with the measured chromaticity and the measured contrast ratio.

TABLE 1

|  |  | Example 1 | Example 2 | Example 3 | Example 4 | Example 5 | Example 6 | Example 7 |
|---|---|---|---|---|---|---|---|---|
| Uppermost layer | Paste Number | P-1 | P-2 | P-3 | P-13 | P-4 | P-12 | P-1 |
|  | $C_U$ | 0.49 | 0.51 | 0.51 | 0.48 | 0.59 | 0.60 | 0.49 |
|  | $L_U$ | 73.6 | 73.2 | 71.7 | 72.7 | 71.6 | 77.6 | 73.6 |
|  | $a_U$ | −1.0 | −1.9 | −2.1 | −0.9 | −1.7 | −1.8 | −1.0 |
|  | $b_U$ | 6.3 | 8.8 | 11.6 | 6.5 | 15.2 | 1.1 | 6.3 |
|  | Linear shrinkage rate (%) | 1.9 | 1.9 | 1.9 | 0.8 | 1.9 | 0.8 | 1.9 |
|  | Heat generated by polymerization (J/g) | 83 | 83 | 83 | 67 | 83 | 77 | 83 |
| Lowermost layer | Paste Number | P-6 | P-4 | P-7 | P-6 | P-6 | P-8 | P-6 |
|  | $C_L$ | 0.60 | 0.59 | 0.60 | 0.60 | 0.60 | 0.74 | 0.60 |
|  | $L_L$ | 73.2 | 71.6 | 69.8 | 73.2 | 73.2 | 68.3 | 73.2 |
|  | $a_L$ | −1.7 | −1.7 | −1.5 | −1.7 | −1.7 | 0.9 | −1.7 |

TABLE 1-continued

|  |  |  |  |  |  |  |  |  |
|---|---|---|---|---|---|---|---|---|
|  | $b_L$ | 11.7 | 15.2 | 17.7 | 11.7 | 11.7 | 27.0 | 11.7 |
|  | Linear shrinkage rate (%) | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 |
|  | Volume ratio (uppermost layer:lowermost layer) | 1:2 | 1:2 | 1:2 | 1:2 | 1:2 | 1:2 | 3:1 |
|  | Color difference ($\Delta E_{UL}$) between uppermost layer and lowermost layer | 5.5 | 6.6 | 6.4 | 5.3 | 3.8 | 27.7 | 5.5 |
|  | Color tone of prosthetic device | AA | AA | AA | AA | A | B | A |
|  | Breakage and cracks during molding of block body | A | A | A | B | A | B | A |
|  | Durability under high temperature and high humidity | A | A | A | A | A | A | A |

|  |  | Example 8 | Example 9 | Comparative Example 1 | Comparative Example 2 | Comparative Example 3 | Comparative Example 4 |
|---|---|---|---|---|---|---|---|
| Uppermost layer | Paste Number | P-13 | P-15 | P-5 | P-12 | P-1 | P-17 |
|  | $C_U$ | 0.48 | 0.49 | 0.28 | 0.60 | 0.49 | 0.49 |
|  | $L_U$ | 72.7 | 73.6 | 70.0 | 77.6 | 73.6 | 73.6 |
|  | $a_U$ | −0.9 | −1.0 | 0.4 | −1.8 | −1.0 | −1.0 |
|  | $b_U$ | 6.5 | 6.3 | 23.4 | 1.1 | 6.3 | 6.3 |
|  | Linear shrinkage rate (%) | 0.8 | 2.1 | 1.9 | 0.8 | 1.9 | 2.2 |
|  | Heat generated by polymerization (J/g) | 67 | 83 | 83 | 77 | 83 | 83 |
| Lowermost layer | Paste Number | P-14 | P-16 | P-8 | P-9 | P-6 | P-18 |
|  | $C_L$ | 0.60 | 0.60 | 0.74 | 0.60 | 0.60 | 0.60 |
|  | $L_L$ | 73.5 | 73.2 | 68.3 | 72.0 | 73.2 | 73.2 |
|  | $a_L$ | −1.8 | −1.7 | 0.9 | −1.7 | −1.7 | −1.7 |
|  | $b_L$ | 10.9 | 11.7 | 27.0 | 15.2 | 11.7 | 11.7 |
|  | Linear shrinkage rate (%) | 1.0 | 2.1 | 1.9 | 1.9 | 1.9 | 2.2 |
|  | Heat generated by polymerization (J/g) | 72 | 83 | 83 | 83 | 83 | 83 |
|  | Volume ratio (uppermost layer:lowermost layer) | 1:2 | 1:2 | 1:2 | 1:2 | 1:14 | 1:2 |
|  | Color difference ($\Delta E_{UL}$) between uppermost layer and lowermost layer | 4.6 | 5.5 | 4.0 | 15.2 | 5.5 | 5.5 |
|  | Color tone of prosthetic device | AA | AA | C | C | C | AA |
|  | Breakage and cracks during molding of block body | A | A | A | B | A | A |
|  | Durability under high temperature and high humidity | A | A | A | A | A | B |

TABLE 2

|  |  | Example 10 | Comparative Example 5 | Example 11 | Comparative Example 6 | Example 12 | Comparative Example 7 |
|---|---|---|---|---|---|---|---|
| Uppermost layer | Paste Number | P-19 | P-20 | P-1 | P-1 | P-1 | P-1 |
|  | $C_U$ | 0.30 | 0.62 | 0.49 | 0.49 | 0.49 | 0.49 |
|  | $L_U$ | 73.6 | 73.6 | 73.6 | 73.6 | 73.6 | 73.6 |
|  | $a_U$ | −1.0 | −1.0 | −1.0 | −1.0 | −1.0 | −1.0 |
|  | $b_U$ | 6.3 | 6.3 | 6.3 | 6.3 | 6.3 | 6.3 |
|  | Linear shrinkage rate (%) | 1.9 | 1.9 | 1.9 | 1.9 | 1.9 | 1.9 |
|  | Heat generated by polymerization (J/g) | 83 | 83 | 83 | 83 | 83 | 83 |
| Lowermost layer | Paste Number | P-6 | P-8 | P-21 | P-22 | P-23 | P-24 |
|  | $C_L$ | 0.60 | 0.74 | 0.90 | 0.92 | 0.55 | 0.53 |
|  | $L_L$ | 73.2 | 68.3 | 73.2 | 73.2 | 73.2 | 73.2 |
|  | $a_L$ | −1.7 | 0.9 | −1.7 | −1.7 | −1.7 | −1.7 |
|  | $b_L$ | 11.7 | 27.0 | 11.7 | 11.7 | 11.7 | 11.7 |
|  | Linear shrinkage rate (%) | 1.9 | 1.9 | 1.9 | 1.9 | 1.9 | 1.9 |
|  | Heat generated by polymerization (J/g) | 83 | 83 | 83 | 83 | 83 | 83 |
| Volume ratio (uppermost layer:lowermost layer) |  | 1:2 | 1:2 | 1:2 | 1:2 | 1:2 | 1:2 |
| Color difference ($\Delta E_{UL}$) between uppermost layer and lowermost layer |  | 5.5 | 21.5 | 5.5 | 5.5 | 5.5 | 5.5 |
| Color tone of prosthetic device |  | B | C | B | C | A | C |
| Breakage and cracks during molding of block body |  | A | A | A | A | A | A |
| Durability under high temperature and high humidity |  | A | A | A | A | A | A |

TABLE 2-continued

|  |  | Example 13 | Comparative Example 8 | Example 14 | Comparative Example 9 |
|---|---|---|---|---|---|
| Uppermost layer | Paste Number | P-25 | P-26 | P-1 | P-1 |
|  | $C_U$ | 0.49 | 0.49 | 0.49 | 0.49 |
|  | $L_U$ | 80.0 | 80.3 | 73.6 | 73.6 |
|  | $a_U$ | −1.0 | −1.0 | −1.0 | −1.0 |
|  | $b_U$ | 6.3 | 6.3 | 6.3 | 6.3 |
|  | Linear shrinkage rate (%) | 1.9 | 1.9 | 1.9 | 1.9 |
|  | Heat generated by polymerization (J/g) | 83 | 83 | 83 | 83 |
| Lowermost layer | Paste Number | P-6 | P-6 | P-27 | P-28 |
|  | $C_L$ | 0.60 | 0.60 | 0.60 | 0.60 |
|  | $L_L$ | 73.2 | 73.2 | 60.0 | 59.8 |
|  | $a_L$ | −1.7 | −1.7 | −1.7 | −1.7 |
|  | $b_L$ | 11.7 | 11.7 | 11.7 | 11.7 |
|  | Linear shrinkage rate (%) | 1.9 | 1.9 | 1.9 | 1.9 |
|  | Heat generated by polymerization (J/g) | 83 | 83 | 83 | 83 |
| Volume ratio (uppermost layer:lowermost layer) |  | 1:2 | 1:2 | 1:2 | 1:2 |
| Color difference ($\Delta E_{UL}$) between uppermost layer and lowermost layer |  | 8.7 | 8.9 | 14.6 | 14.8 |
| Color tone of prosthetic device |  | A | C | A | C |
| Breakage and cracks during molding of block body |  | A | A | A | A |
| Durability under high temperature and high humidity |  | A | A | A | A |

TABLE 3

|  |  | Example 15 | Comparative Example 10 | Example 16 | Comparative Example 11 | Example 17 | Comparative Example 12 | Example 18 | Comparative Example 13 |
|---|---|---|---|---|---|---|---|---|---|
| Uppermost layer | Paste Number | P-29 | P-30 | P-1 | P-1 | P-33 | P-34 | P-1 | P-1 |
|  | $C_U$ | 0.49 | 0.49 | 0.49 | 0.49 | 0.49 | 0.49 | 0.49 | 0.49 |
|  | $L_U$ | 73.6 | 73.6 | 73.6 | 73.6 | 73.6 | 73.6 | 73.6 | 73.6 |
|  | $a_U$ | 2.0 | 2.1 | −1.0 | −1.0 | −1.0 | −1.0 | −1.0 | −1.0 |
|  | $b_U$ | 6.3 | 6.3 | 6.3 | 6.3 | 0.0 | −0.1 | 6.3 | 6.3 |
|  | Linear shrinkage rate (%) | 1.9 | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 | 83 |
| Lowermost layer | Paste Number | P-6 | P-6 | P-31 | P-32 | P-6 | P-6 | P-35 | P-36 |
|  | $C_L$ | 0.60 | 0.60 | 0.60 | 0.60 | 0.60 | 0.60 | 0.60 | 0.60 |
|  | $L_L$ | 73.2 | 73.2 | 73.2 | 73.2 | 73.2 | 73.2 | 73.2 | 73.2 |
|  | $a_L$ | −1.7 | −1.7 | −3.0 | −3.2 | −1.7 | −1.7 | −1.7 | −1.7 |
|  | $b_L$ | 11.7 | 11.7 | 11.7 | 11.7 | 11.7 | 11.7 | 30.0 | 30.2 |
|  | Linear shrinkage rate (%) | 1.9 | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 | 83 |
| Volume ratio (uppermost layer:lowermost layer) |  | 1:2 | 1:2 | 1:2 | 1:2 | 1:2 | 1:2 | 1:2 | 1:2 |
| Color difference ($\Delta E_{UL}$) between uppermost layer and lowermost layer |  | 6.6 | 6.6 | 5.8 | 5.8 | 11.7 | 11.8 | 23.7 | 23.9 |
| Color tone of prosthetic device |  | A | C | A | C | A | C | B | C |
| Breakage and cracks during molding of block body |  | A | A | A | A | A | A | A | A |
| Durability under high temperature and high humidity |  | A | A | A | A | A | A | A | A |

TABLE 4

|  |  | Example 19 | Example 20 | Example 21 | Example 22 | Example 23 | Example 24 | Example 25 |
|---|---|---|---|---|---|---|---|---|
| Uppermost layer | Paste Number | P-37 | P-1 | P-1 | P-1 | P-1 | P-3 | P-3 |
|  | $C_U$ | 0.57 | 0.49 | 0.49 | 0.49 | 0.49 | 0.51 | 0.51 |
|  | $L_U$ | 71.6 | 73.6 | 73.6 | 73.6 | 73.6 | 71.7 | 71.7 |
|  | $a_U$ | −1.7 | −1.0 | −1.0 | −1.0 | −1.0 | −2.1 | −2.1 |
|  | $b_U$ | 15.2 | 6.3 | 6.3 | 6.3 | 6.3 | 11.6 | 11.6 |
|  | Linear shrinkage rate (%) | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 |
| Lowermost layer | Paste Number | P-6 | P-38 | P-39 | P-40 | P-41 | P-42 | P-43 |
|  | $C_L$ | 0.60 | 0.64 | 0.66 | 0.60 | 0.60 | 0.74 | 0.74 |
|  | $L_L$ | 73.2 | 73.2 | 73.2 | 73.6 | 73.6 | 69.2 | 68.3 |

TABLE 4-continued

|  |  | Example 19 | Example 20 | Example 21 | Example 22 | Example 23 | Example 24 | Example 25 |
|---|---|---|---|---|---|---|---|---|
|  | $a_L$ | −1.7 | −1.7 | −1.7 | −1.0 | −1.0 | 0.0 | 0.0 |
|  | $b_L$ | 11.7 | 11.7 | 11.7 | 6.3 | 6.2 | 26.2 | 27.0 |
|  | Linear shrinkage rate (%) | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 |
| Volume ratio (uppermost layer:lowermost layer) |  | 1:2 | 1:2 | 1:2 | 1:2 | 1:2 | 1:2 | 1:2 |
| Color difference ($\Delta E_{UL}$) between uppermost layer and lowermost layer |  | 3.8 | 5.5 | 5.5 | 0.0 | 0.1 | 15.0 | 15.9 |
| Color tone of prosthetic device |  | A | AA | A | A | AA | A | B |
| Breakage and cracks during molding of block body |  | A | A | A | A | A | A | A |
| Durability under high temperature and high humidity |  | A | A | A | A | A | A | A |

TABLE 5

|  |  | Example 26 | Example 27 | Example 28 | Example 29 | Example 30 | Example 31 | Example 32 | Example 33 |
|---|---|---|---|---|---|---|---|---|---|
| Uppermost layer | Paste Number | P-1 | P-1 | P-1 | P-1 | P-13 | P-1 | P-1 | P-1 |
|  | $C_U$ | 0.49 | 0.49 | 0.49 | 0.49 | 0.48 | 0.49 | 0.49 | 0.49 |
|  | $L_U$ | 73.6 | 73.6 | 73.6 | 73.6 | 72.7 | 73.6 | 73.6 | 73.6 |
|  | $a_U$ | −1.0 | −1.0 | −1.0 | −1.0 | −0.9 | −1.0 | −1.0 | −1.0 |
|  | $b_U$ | 6.3 | 6.3 | 6.3 | 6.3 | 6.5 | 6.3 | 6.3 | 6.3 |
|  | Linear shrinkage rate (%) | 1.9 | 1.9 | 1.9 | 1.9 | 0.8 | 1.9 | 1.9 | 1.9 |
|  | Heat generated by polymerization (J/g) | 83 | 83 | 83 | 83 | 67 | 83 | 83 | 83 |
| Lowermost layer | Paste Number | P-6 | P-6 | P-6 | P-6 | P-41 | P-44 | P-45 | P-46 |
|  | $C_L$ | 0.60 | 0.60 | 0.60 | 0.60 | 0.60 | 0.60 | 0.60 | 0.60 |
|  | $L_L$ | 73.2 | 73.2 | 73.2 | 73.2 | 73.2 | 73.2 | 73.2 | 73.2 |
|  | $a_L$ | −1.7 | −1.7 | −1.7 | −1.7 | −1.7 | −1.7 | −1.7 | −1.7 |
|  | $b_L$ | 11.7 | 11.7 | 11.7 | 11.7 | 11.7 | 11.7 | 11.7 | 11.7 |
|  | Linear shrinkage rate (%) | 1.9 | 1.9 | 1.9 | 1.9 | 1.8 | 1.9 | 1.9 | 1.9 |
|  | Heat generated by polymerization (J/g) | 83 | 83 | 83 | 83 | 83 | 53 | 33 | 30 |
| Volume ratio (uppermost layer:lowermost layer) |  | 1:4 | 1:3 | 1:1 | 2:1 | 1:2 | 1:2 | 1:2 | 1:2 |
| Color difference ($\Delta E_{UL}$) between uppermost layer and lowermost layer |  | 5.5 | 5.5 | 5.5 | 5.5 | 5.3 | 5.5 | 5.5 | 5.5 |
| Color tone of prosthetic device |  | A | AA | AA | A | AA | A | A | A |
| Breakage and cracks during molding of block body |  | A | A | A | A | A | A | A | B |
| Durability under high temperature and high humidity |  | A | A | A | A | A | A | A | A |

TABLE 6

|  |  | Example 34 | Example 35 | Example 36 | Example 37 | Example 38 | Example 39 | Example 40 | Example 41 |
|---|---|---|---|---|---|---|---|---|---|
| Uppermost layer | Paste Number | P-1 | P-4 | P-1 | P-47 | P-47 | P-1 | P-1 | P-1 |
|  | $C_U$ | 0.49 | 0.59 | 0.49 | 0.40 | 0.40 | 0.49 | 0.49 | 0.49 |
|  | $L_U$ | 73.6 | 71.6 | 73.6 | 73.6 | 73.6 | 73.6 | 73.6 | 73.6 |
|  | $a_U$ | −1.0 | −1.7 | −1.0 | −1.0 | −1.0 | −1.0 | −1.0 | −1.0 |
|  | $b_U$ | 6.3 | 15.2 | 6.3 | 6.3 | 6.3 | 6.3 | 6.3 | 6.3 |
|  | Linear shrinkage rate (%) | 1.9 | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 | 83 |
| Middle layer | Paste Number | P-10 | P-7 | P-6 | P-48 | P-49 | P-50 | P-51 | P-10 |
|  | $C_M$ | 0.55 | 0.60 | 0.60 | 0.44 | 0.45 | 0.65 | 0.66 | 0.55 |
|  | $L_M$ | 72.5 | 69.8 | 73.2 | 72.5 | 72.5 | 73.2 | 73.2 | 72.5 |
|  | $a_M$ | −1.4 | −1.5 | −1.7 | −1.4 | −1.4 | −1.7 | −1.7 | −1.4 |
|  | $b_M$ | 7.4 | 17.7 | 11.7 | 7.4 | 7.4 | 11.7 | 11.7 | 7.4 |
|  | Linear shrinkage rate (%) | 1.9 | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 | 83 |
| Lower most layer | Paste Number | P-6 | P-11 | P-8 | P-6 | P-6 | P-8 | P-8 | P-6 |
|  | $C_L$ | 0.60 | 0.61 | 0.74 | 0.60 | 0.60 | 0.74 | 0.74 | 0.60 |
|  | $L_L$ | 73.2 | 67.5 | 68.3 | 73.2 | 73.2 | 68.3 | 68.3 | 73.2 |
|  | $a_L$ | −1.7 | −1.7 | 0.9 | −1.7 | −1.7 | 0.9 | 0.9 | −1.7 |
|  | $b_L$ | 11.7 | 16.9 | 27.0 | 11.7 | 11.7 | 27.0 | 27.0 | 11.7 |
|  | Linear shrinkage rate (%) | 1.9 | 1.9 | 1.9 | 1.9 | 1.9 | 1.9 | 1.9 | 1.9 |
|  | Heat generated by polymerization (J/g) | 83 | 83 | 83 | 83 | 83 | 83 | 83 | 83 |
| Volume ratio (uppermost layer:lowermost layer) |  | 1:2 | 1:2 | 1:2 | 1:2 | 1:2 | 1:2 | 1:2 | 3:1 |
| Volume ratio (uppermost layer:middle layer) |  | 1:1 | 1:1 | 1:1 | 1:1 | 1:1 | 1:1 | 1:1 | 1.5:1 |
| Volume ratio (middle layer:lowermost layer) |  | 1:2 | 1:2 | 1:2 | 1:2 | 1:2 | 1:2 | 1:2 | 2:1 |
| Color difference ($\Delta E_{UM}$) between uppermost layer and middle layer |  | 1.6 | 3.1 | 5.5 | 1.6 | 1.6 | 5.5 | 5.5 | 1.6 |

TABLE 6-continued

|  | Example 34 | Example 35 | Example 36 | Example 37 | Example 38 | Example 39 | Example 40 | Example 41 |
|---|---|---|---|---|---|---|---|---|
| Color difference ($\Delta E_{ML}$) between middle layer and lowermost layer | 4.4 | 2.4 | 16.3 | 4.4 | 4.4 | 16.3 | 16.3 | 4.4 |
| Color tone of prosthetic device | AA | A | A | A | AA | A | B | A |
| Breakage and cracks during molding of block body | A | A | A | A | A | A | A | A |
| Durability under high temperature and high humidity | A | A | A | A | A | A | A | A |

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present disclosure relates to a resin material for dental milling and machining constituted with a plurality of layers different from each other in transparency and color tone, for preparing dental prosthetic devices (crowns, bridges). It is possible to provide a dental crown prosthetic device having high aesthetic quality, in spite of a relatively simple layer structure.

What is claimed is:

1. A multilayer resin material for dental milling and machining, comprising an inorganic filler in a content of 40% by weight or more and a plurality of layers different in transparency and color tone from each other, wherein the thickness of the uppermost layer (U) and the thickness of the lowermost layer (L) are each 1 mm or more, the contrast ratios (uppermost layer: $C_U$, lowermost layer: $C_L$) as indices for the transparency of the uppermost layer (U) and the transparency of the lowermost layer (L) satisfy the following relations:

$0.30 \leq C_U \leq 0.60$ $0.55 \leq C_L \leq 0.90$ $C_U \leq C_L$ and the chromaticities (uppermost layer: $L_U \cdot a_U \cdot b_U$, lowermost layer: $L_L \cdot a_L \cdot b_L$) based on the L*a*b* colorimetric system as the indices of the color tones in the uppermost layer (U) and the lowermost layer (L) satisfy the following relations:

$60 \leq L_U \cdot L_L \leq 80$ $-3 \leq a_U \cdot a_L \leq 2$ $0 \leq b_U \cdot b_L \leq 30$.

2. The multilayer resin material for dental milling and machining according to claim 1, wherein the volume ratio between the uppermost layer (U) and the lowermost layer (L) is 1:3 to 1:1.

3. The multilayer resin material for dental milling and machining according to claim 1, wherein the thickness of a middle layer (M) positioned between the uppermost layer (U) and the lowermost layer (L) is 0.5 mm or more; and the contrast ratio ($C_M$) as an index for the transparency in the middle layer (M) satisfies the following relations:

$0.45 \leq C_M \leq 0.65$ $C_U < C_M < C_L$ and the chromaticity (middle layer: $L_M \cdot a_M \cdot b_M$) based on the L*a*b* colorimetric system as the index for the color tone in the middle layer (M) satisfies the following relations:

$60 \leq L_M \leq 80$ $-3 \leq a_M \leq 2$ $0 \leq b_M \leq 30$.

4. The multilayer resin material for dental milling and machining according to 3, wherein at least one of the volume ratio between the uppermost layer (U) and the middle layer (M), the volume ratio between the middle layer (M) and the lowermost layer (L) and the volume ratio between the uppermost layer (U) and the lowermost layer (L) is 1:3 to 1:1.

5. The multilayer resin material for dental milling and machining according to claim 3, wherein the contrast ratio difference ($|C_U - C_L|$) between the uppermost layer (U) and the lowermost layer (L) is 0.03 to 0.15.

6. The multilayer resin material for dental milling and machining according to claim 3, wherein the color difference $\Delta E_{UL}$ between the uppermost layer (U) and the lowermost layer (L) is 0.1 to 15.0.

7. The multilayer resin material for dental milling and machining according to claim 3, wherein the contrast ratio difference ($|C_U - C_M|$) between the uppermost layer (U) and the middle layer (M) is 0.03 to 0.15, and the contrast ratio difference ($|C_M - C_L|$) between the middle layer (M) and the lowermost layer (L) is 0.03 to 0.15.

8. The multilayer resin material for dental milling and machining according to claim 7, wherein the color difference $\Delta E_{UL}$ between the uppermost layer (U) and the lowermost layer (L) is 0.1 to 15.0.

9. The multilayer resin material for dental milling and machining according to claim 7, wherein the color difference $\Delta E_{UM}$ between the uppermost layer (U) and the middle layer (M) and the color difference $\Delta E_{ML}$ between the middle layer (M) and the lowermost layer (L) are 0.1 to 15.0.

10. The multilayer resin material for dental milling and machining according to 4, wherein at least one of the volume ratio between the uppermost layer (U) and the middle layer (M), the volume ratio between the middle layer (M) and the lowermost layer (L) and the volume ratio between the uppermost layer (U) and the lowermost layer (L) is 1:3 to 1:1.

11. The multilayer resin material for dental milling and machining according to claim 3, wherein the color difference $\Delta E_{UM}$ between the uppermost layer (U) and the middle layer (M) and the color difference $\Delta E_{ML}$ between the middle layer (M) and the lowermost layer (L) are 0.1 to 15.0.

12. The multilayer resin material for dental milling and machining according to 11, wherein at least one of the volume ratio between the uppermost layer (U) and the middle layer (M), the volume ratio between the middle layer (M) and the lowermost layer (L) and the volume ratio between the uppermost layer (U) and the lowermost layer (L) is 1:3 to 1:1.

13. The multilayer resin material for dental milling and machining according to claim 1, wherein the contrast ratio difference ($|C_U - C_L|$) between the uppermost layer (U) and the lowermost layer (L) is 0.03 to 0.15.

14. The multilayer resin material for dental milling and machining according to claim 13, wherein the color difference $\Delta E_{UL}$ between the uppermost layer (U) and the lowermost layer (L) is 0.1 to 15.0.

15. The multilayer resin material for dental milling and machining according to claim 13, wherein the volume ratio between the uppermost layer (U) and the lowermost layer (L) is 1:3 to 1:1.

16. The multilayer resin material for dental milling and machining according to claim 1, wherein the color difference $\Delta E_{UL}$ between the uppermost layer (U) and the lowermost layer (L) is 0.1 to 15.0.

17. The multilayer resin material for dental milling and machining according to claim 16, wherein the volume ratio between the uppermost later (U) and the lowermost layer (L) is 1:3 to 1:1.

18. A method for producing the multilayer resin material for dental milling and machining according to claim 1, produced by stacking uncured paste-like substances in layers and sequentially polymerizing and curing the stacked substances, wherein the difference or differences in the linear polymerization shrinkage rate between the respective layers are 1.0% or less, and/or the difference or differences in the heat generated by polymerization between the respective layers are 50 J/g or less.

* * * * *